United States Patent [19]

Reed et al.

[11] Patent Number: 5,446,132

[45] Date of Patent: Aug. 29, 1995

[54] THROMBIN-ACTIVATED PLATELET PROTEIN-2 (TAPP-2)

[75] Inventors: Guy L. Reed, Winchester, Mass.; Gary R. Matsueda, Princeton, N.J.

[73] Assignee: The General Hospital Corporation, Boston, Mass.

[21] Appl. No.: 86,472

[22] Filed: Oct. 1, 1992

Related U.S. Application Data

[63] Continuation-in-part of Ser. No. 768,043, Oct. 1, 1992, abandoned.

[51] Int. Cl.$^6$ .................... C07K 14/435; C07K 14/46; C07K 14/47; C07K 14/52
[52] U.S. Cl. ..................... 530/350; 530/350; 436/501; 435/7.2
[58] Field of Search ................ 530/380, 350; 436/501; 435/7.2

[56] References Cited

U.S. PATENT DOCUMENTS 4,783,330  11/1988  Furie et al. ............... 424/1.1

FOREIGN PATENT DOCUMENTS 0182634  5/1986  European Pat. Off. ...... C07K 15/00
0187658  7/1986  European Pat. Off. ...... A61K 39/39

OTHER PUBLICATIONS

Bennett, Joel S., "The Molecular Biology of Platelet Membrane Proteins", *Semimars in Hematology* 27(2):186:–204 (Apr. 1990).

Bode, Christoph et al., "Antibody-Directed Urokinase: A Specific Fibrinolytic Agent", *Science* 229:765–767 (Aug. 23, 1985).

Febbraio, Maria et al., "Identification and Characterization of LAMP-1 as an Activation-dependent Platelet Surface Glycoportein", *J. Biol. Chem.* 265(30):18531–18537 (Oct. 25, 1990).

Frelinger III, Andrew L. et al., "Selective Inhibition of Integrin Function by Antibodies Specific for Ligand-occupied Receptor Conformers", *J Biol. Chem.* 265(11):6346–6352 (Apr. 15, 1990).

Gerrard, J. M. et al., "Identification of a Platelet Dense Granule Membrane Protein That Is Deficient in a Patient with the Hermansky–Pudlak Syndrome", *Blood* 77(1):101–112 (Jan. 1, 1991).

Gogstad, Geir O. et al., "Platelet Factor XIII Is an Active Enzyme After Solubilization and Crossed Immunoelectrophoresis", *Thrombosis Research* 29(2):237–241 (1983).

Gralnick, H. R. et al., "A Monoclonal Antibody which Recognizes a New Activation Dependent Antigen and Results in the Enhanced Binding of Fibrinogen to Activated Platelets", *Blood* 76(Suppl. 1):457A, Abstracts No. 1818 (1990).

Hayward, Catherine P. M. et al., "p-155 A Multimeric Platelet Protein That Is Expressed on Activated Platelets", *J. Biol. Chem.* 266(11):7114–7120 (Apr. 15, 1991).

Hawyard, Catherine P. M. et al., "P-155: A Novel, Multimeric Platelet Protein That Is Released With Platelet Activation and Expressed on the Surface of Activated Platelets", *Blood* 76(Suppl. 1):458A, Abstract No. 1824 (1990).

(List continued on next page.)

*Primary Examiner*—Garnette D. Draper
*Assistant Examiner*—Elizabeth C. Kemmerer
*Attorney, Agent, or Firm*—Sterne, Kessler, Goldstein & Fox

[57] ABSTRACT

The present invention provides a thrombin-activated platelet protein (TAPP). The protein is selectively expressed on the surface of thrombin-activated platelets. Antibodies which selectively bind to the thrombin-activated platelet protein are also provided. These compositions find use in the detection and treatment of blood clots.

2 Claims, 4 Drawing Sheets

OTHER PUBLICATIONS

Hsu-Lin Shu-Chun et al., "A Platelet Membrane Protein Expressed during Platelet Activation and Secretion", *J. Biol. Chem.* 259(14):9121-9126 (Jul. 25, 1984).

Johnston, Geoffrey I. et al., "Cloning of GMP-140, a Granule Membrane Protein of Platelets and Endothelium: Sequence Similarity to Proteins Involved in Cell Adhesion and Inflammation", *Cell* 56:1033-1044 (Mar. 24, 1989).

Larsen, Eric et al., "PADGEM Protein: A Receptor That Mediates the Interaction of Activated Platelets with Neutrophils and Monocytes", *Cell* 59:305-312 (Oct. 20, 1989).

McEver, Rodger, et al., "A Monoclonal Antibody to a Membrane Glycoprotein Binds Only to Activated Platelets", *J. Biol. Chem.* 259(15):9799-9804 (Aug. 10, 1984).

Morrison, Sherie L., "Transfectomas Provide Novel Chimeric Antibodies", *Science* 229:1202-1207 (Sep. 20, 1985).

Nieuwenhuis, H. Karel et al., "Studies With a Monoclonal Antibody Against Activated Platelets: Evidence That a Secreted 53,000-Molecular Weight Lysosome-like Granule Protein Is Exposed on the Surface of Activated Platelets in the Circulation", *Blood* 70(3):838-845 (Sep. 1987).

Savage, Brian et al., "Thrombin-Induced Increase in Surface Expression of Epitopes on Platelet Membrane Glycoprotein IIb/IIIa Complex and GMP-140 Is A Function of Platelet Age", *Blood* 74(3):1007-1014 (Aug. 15, 1989).

Sutherland, D. Robert et al., "Identification of a Cell-Surface Antigen Associated with Activated T Lymphoblasts and Activated Platelets", *Blood* 77(1):84-93 (Jan. 1, 1991).

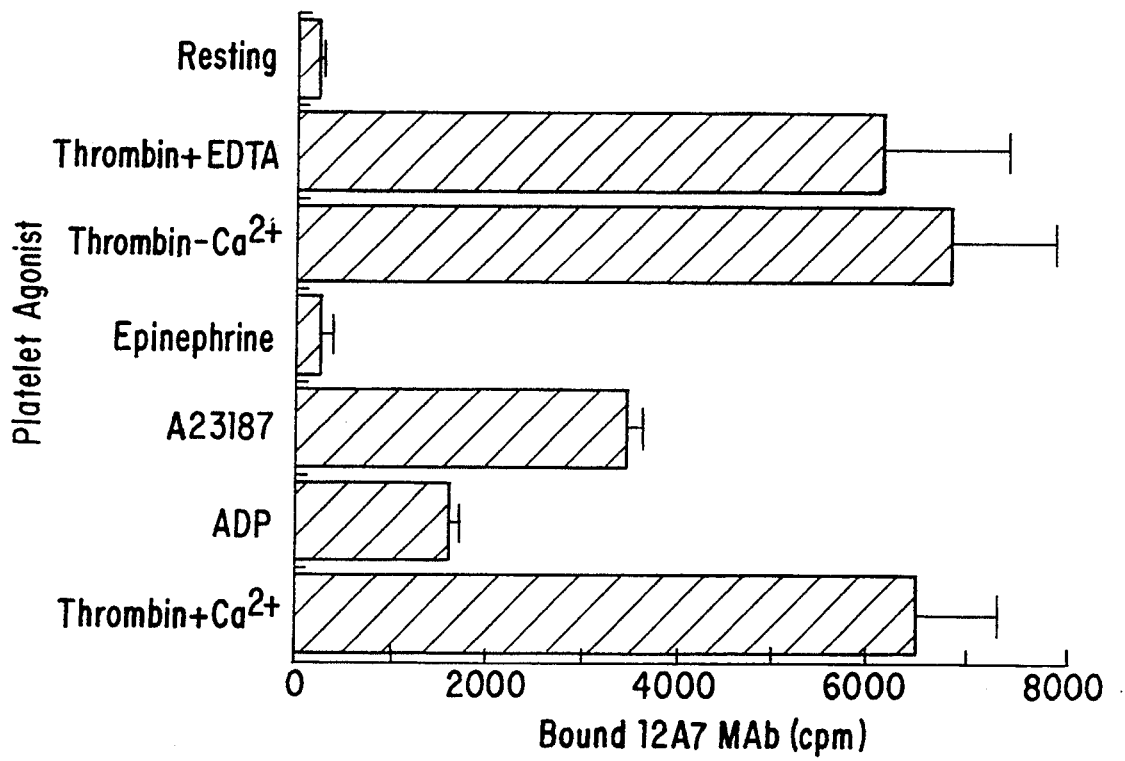
FIG. 4
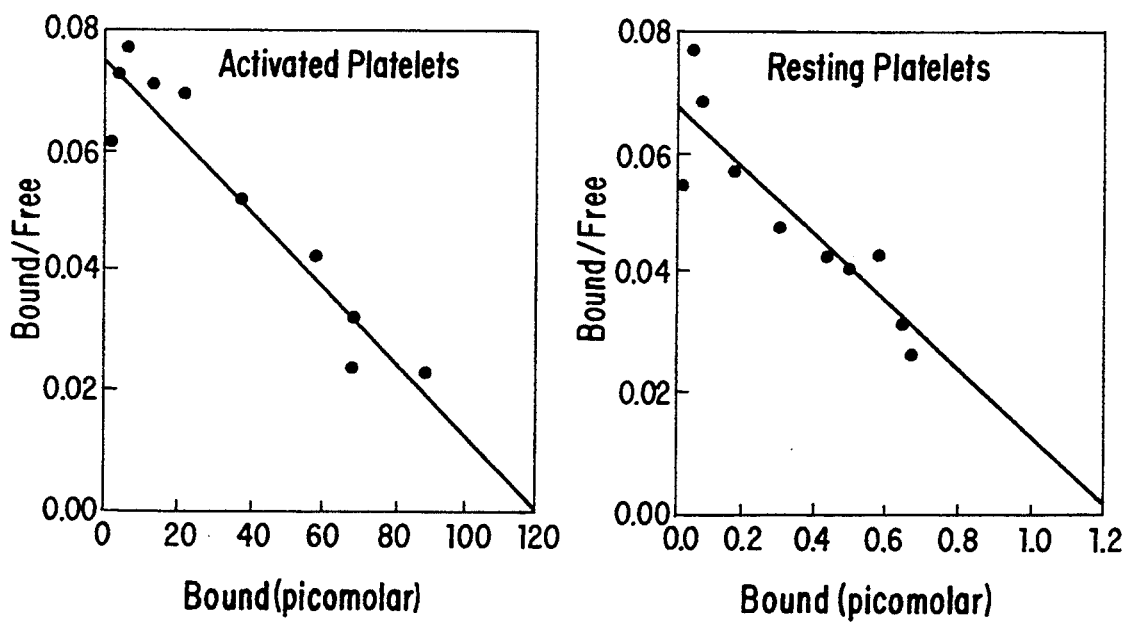
FIG. 5A
FIG. 5B

THROMBIN-ACTIVATED PLATELET PROTEIN-2 (TAPP-2)

STATEMENT OF GOVERNMENT RIGHTS IN THE INVENTION

Part of the work performed during development of this invention utilized U.S. Government funds. The U.S. Government has certain rights in this invention.

CROSS REFERENCE TO RELATED APPLICATION

This application is a continuation-in-part of U.S. application Ser. No. 07/768,043, filed Oct. 1, 1992, now abandoned.

FIELD OF THE INVENTION

The present invention relates to the detection and treatment of myocardial infarction, deep venous thrombosis, pulmonary emboli, cerebrovascular thrombosis, or any thrombolytic process within a patient.

BACKGROUND OF THE INVENTION

Platelets are anucleate cells which circulate in the blood in both resting and active forms. Platelets are responsible for the formation of the hemostatic blood that provides the primary defense against hemorrhage following vascular trauma. Upon stimulation and degranulation, activated platelets are recruited into growing thrombi or cleared rapidly from the blood circulation. In the formation of growing thrombi, platelets may contact with and spread upon the subendothelial matrix in a process termed platelet adhesion. The resulting layer of adherent platelets provides the foundation for the hemostatic blood.

There is an increasing understanding of the mechanisms responsible for the activation, secretion, and aggregation of platelets. However, there is still little firm data on the molecular alterations to the platelet membrane that accompany or mediate these three processes. The identification and characterization of proteins that are selectively expressed on the surface of activated platelets or that undergo functional changes during platelet activation may help clarify the steps involved in these processes. However, the changes on the platelet membrane that accompany platelet activation have been partially identified. Stable platelet adhesion requires an interaction between the platelet membrane glycoprotein Ib/IX complex and the multimeric protein von Willebrand factor present in the subendothelial matrix.

Monoclonal antibodies have been used to identify proteins thought to be specifically expressed on the surface of activated platelets (Hsu-Lin et al., *J. Biol. Chem.* 259:9121–9126 (1984); McEver and Martin, *J. Biol. Chem.* 259:9799–9804 (1984); Nieuwenhuis et al., *Blood* 70:838–845 (1987); Gralnick et al., *Blook* 76 (Suppl. 1):457A (1990); Hayward et al., *J. Biol. Chem.* 266:7114–7120 (1991)). The best characterized of these proteins, GMP-140 (PADGEM, CD62), is also apparently expressed on the surface of activated endothelial cells (Johnston et al., *Cell* 56:1033–1044 (1989)). Analysis of the GMP-140 cDNA sequence suggests that the protein is one of the family of lectin-like cell adhesion molecules (Johnston et al., *Cell* 56:1033–1044 (1989)). GMP-140 also appears to be involved in the interaction between activated platelets and neutrophils or monocytes (Larsen et al., *Cell* 59:305–312 (1989)). Thus the identification of cellular, activation-dependent antigens in platelets may also help to illuminate the alterations that occur during activation in other cells—e.g. lymphocytes, endothelial cells, neutrophils, and monocytes. Identification of these antigens may also elucidate activation-dependent interactions between different cells or between cells and specific functional ligands.

The identification of other antigens specifically expressed on the surface of activated platelets may help elucidate some of the molecular changes that occur during platelet activation, particularly those responsible for changing the platelet from a quiescent cell to a fully adherent thrombocyte. Perhaps the best example of information derived from the study of platelet surface proteins is the research on the glycoproteins IIb/IIIa. Studies of the GPIIb/IIIa glycoproteins, using specific ligands and monoclonal antibodies, are beginning to elucidate the molecular rearrangements that occur in the GPIIb/IIIa complex, with regard to conformation, density, etc., which are responsible for its conversion to a fully competent "receptor" that mediates platelet aggregation (reviewed in Bennett, J.S., *Semin. Hematol.* 27:186–204 (1990)). Although these studies have significantly enlarged our grasp of the mechanisms of platelet aggregation, our understanding of other platelet events remains less complete.

The initiating event of many myocardial infarctions (heart attacks) is the hemorrhage into atherosclerotic plaque. Such hemorrhage often results in the formation of a thrombus (or blood clot) in the coronary artery which supplies the infarct zone (i.e., an area of coagulation necrosis which results from an obstruction of blood circulation). This thrombus is composed of a combination of fibrin and blood platelets. The formation of a thrombin-platelet clot has serious clinical ramifications. The degree and duration of the occlusion caused by the fibrin-platelet clot determines the mass of the infarct zone and the extent of damage.

The primary goal of current treatment for myocardial infarction involves the rapid dissolution of the occluding thrombus and the restoration of blood flow (reperfusion). A successful therapy must be capable of sustained effect so that reformation of the clot does not occur after the cessation of therapy. If the fibrin-platelet clot is able to reform, then the affected artery may become reoccluded.

Treatment with thrombolytic agents can often successfully restore coronary blood flow rapidly enough to interrupt myocardial infarction. Unfortunately, the dissolved fibrin-platelet clot has been found to reform after cessation of such thrombolytic therapy in a substantial number of patients. This reformation may result in the reocclusion of the affected blood vessels, and is, therefore, of substantial concern.

A thrombolytic agent is a medicament capable of lysing the fibrin-platelet thrombus, and thereby permitting blood to again flow through the affected blood vessel. Such agents include streptokinase, prourokinase, urokinase, and tissue-type plasminogen activator. See, for example, Ganz et al., *J. Amer. Coll. Cardiol.* 1:1247–1253 (1983); Rentrop et al. *Amer. J. Cardiol.* 54:29E–31E (1984); and Gold et al., *Amer. J. Cardiol.* 53:122C–125C (1984).

Clot lysis is mediated by plasmin vv. Under natural conditions, plasminogen is converted to plasmin by tissue plasminogen activator (t-PA). Activation occurs on the fibrin surface, thus confining proteolytic activity to the appropriate site. After plasmin is set free into the circulation, it is rapidly combined with natural inhibitors. An activation of plasmin is the final and necessary step in the process of protecting against undesirable proteolysis. Such plasmin inhibitors include α-2 antiplasmin, α-2 microglobulin and α-1 antitrypsin, all glycoproteins. α-2 antiplasmin has a much higher affinity for plasmin than α-2-macroglobulin and binds specifically to plasmin in a 1:1 ratio. Therefore, clot lysis by the administration of t-PA is limited by the rapid and irreversible inactivation of plasmin by plasmin inhibitors.

All available thrombolytic agents still suffer significant shortcomings, including the need for large doses to be therapeutically efficient, a limited fibrin-specificity, residual toxicity in terms of bleeding complications. Cardiovascular disease is still a major cause of disability. All current agents are associated with thrombolytic reocclusion of blood vessels during or after therapy. Therefore, there remains a need for additional agents which can be utilized alone or in combination with known therapeutic agents. Improvements in thrombolytic therapy which enhance clot lysis, or target the thrombolytic agent to the blood clot are needed.

RELATED ART

An overview on the molecular biology of platelet membrane proteins can be found in *Seminars in Hematology* 27:186–204 (1990). Hsu-Lin et al., *J. Biol. Chem.* 259:9121–9126 (1986) describe a platelet membrane protein expressed during platelet activation and secretion. Other references which describe platelet proteins include Savage et al., *Blood* 74:1007–1014 (1989); Hayward, *Blood* 76 (Suppl. 1):458A (1990); Gralnick et al., *Blood* 76 (Suppl. 1):457A (1990); and Larsen et al., *Cell* 59:305–312 (1989). The cloning of GMP-140 is described by Johnston et al., *Cell* 56:1033–1044 (1989).

SUMMARY OF THE INVENTION

The present invention is drawn to a thrombin-activated platelet protein (TAPP) and its uses. Two such proteins are provided by the invention, TAPP-1 and TAPP-2. The protein is selectively expressed on the surface of thrombin-activated platelets. The invention is further drawn to antibodies which specifically bind to the thrombin-activated platelet protein. These compositions find use in the in vitro or in vivo detection and treatment of activated platelets, blood clots, myocardial infarction, deep venous thrombosis, pulmonary emboli, cerebrovascular thrombosis, disseminated intravascular coagulation, or other thrombotic processes.

DESCRIPTION OF THE FIGURES

FIG. 4 demonstrates the expression of TAPP-2 on platelets stimulated by different agonists. Platelets were incubated with various agonists, with or without Ca$^{2+}$ or EDTA and then fixed by paraformaldehyde. The fixed platelets were washed and incubated with $^{125}$I-MAb 12A7 (50,000 cpm), with or without unlabeled MAb 12A7 (0.5 ug) added as an inhibitor to estimate nonspecific binding. After 45 min. the platelet samples were again washed, spun, and aspirated. The platelet pellet was counted to determine the amount of bound MAb 12A7. The mean and SEM of triplicate observations are shown.

FIG. 5 shows the results of saturation binding studies of MAb 12A7 to thrombin-activated and resting platelets. Pooled thrombin-activated platelets ($5\times10^6$ cells) or resting platelets ($1.29\times10^8$ cells) were incubated with $^{125}$I-MAb 12A7 45 minutes at room temperature. After washing with cold, modified Tyrode's buffer and centrifugation, the amount of bound antibody was determined by gamma scintillation counting. The Scatchard transformation of the binding data as analyzed with the Ligand program is shown. MAb 12A7 bound to a single class of molecules with 14,200±1100 copies per activated platelet (r=0.95) and 290±30 copies per resting platelet (r=0.90).

DETAILED DESCRIPTION OF THE INVENTION

Figure 1:
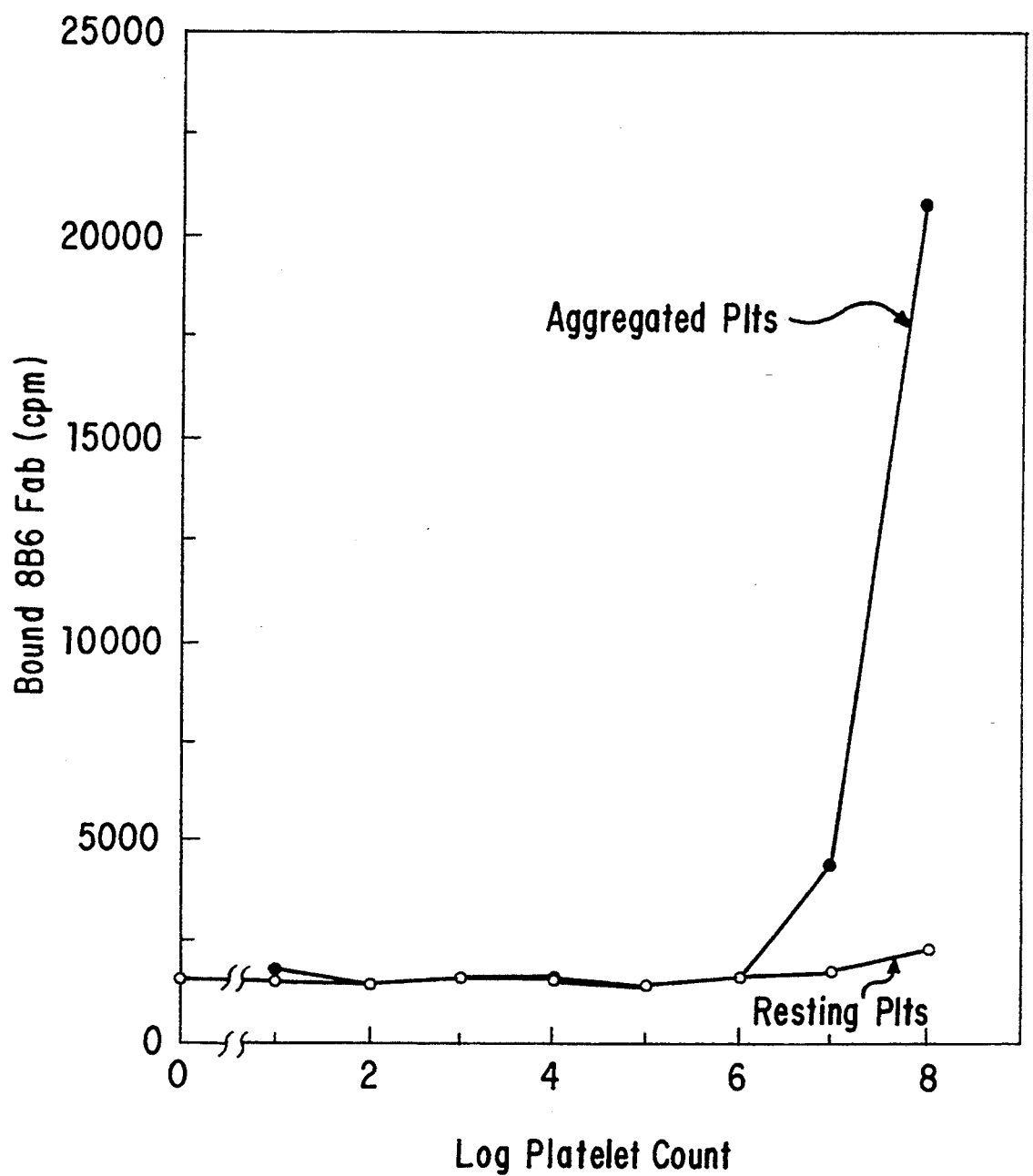
FIG. 1 shows the comparative binding of MAb 8B6 Fab to resting and thrombin-activated human platelets. Pooled human platelets were separated from plasma by gel chromatography with modified Tyrode's buffer (without calcium and magnesium) and counted. After counting the platelets were divided and one portion was aggregated by the addition of thrombin (0.15 U/ml) and calcium (4 mM). The thrombin-activated or resting platelets were diluted into 200 μl of a modified Tyrode's buffer with calcium and magnesium or with EDTA. Radioiodinated MAb 8B6 Fab (20 μl, 180,000 cpm) was added to each tube and allowed to incubate for 1 hr at room temperature. After washing with 3 ml of the corresponding modified Tyrode's buffer, centrifugation and aspiration, the bound antibody was detected by gamma scintillation counting.
Figure 2:
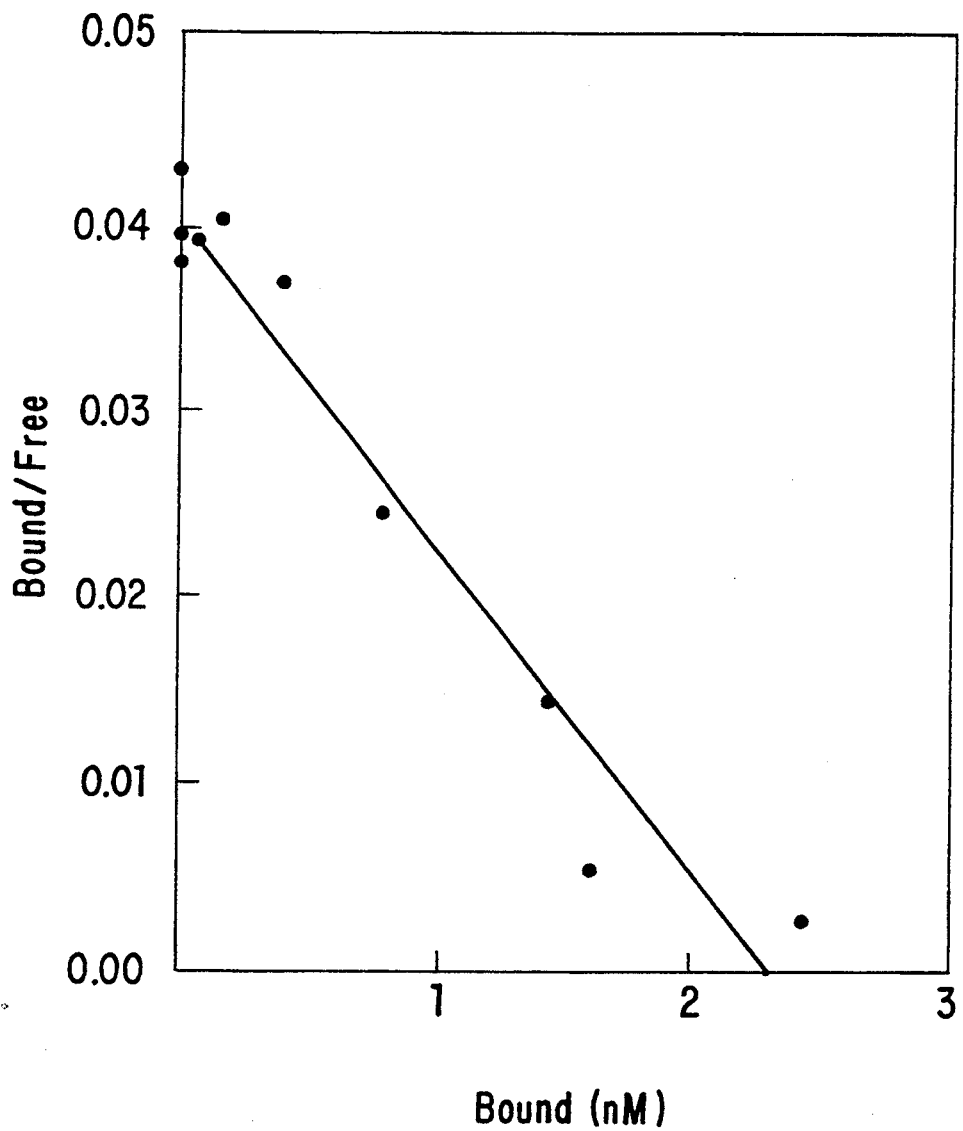
FIG. 2 depicts the results from saturation binding studies of MAb 8B6 Fab to thrombin-activated and resting platelets. Pooled thrombin-activated human platelets ($5\times10^6$) were incubated with radiolabeled MAb 8B6 Fab (0.7 nM) and various amounts of cold MAb 8B6 Fab (1 nM–0.9 μM) for 30 minutes at room temperature. After washing with cold, modified Tyrode's buffer and centrifugation, the amount of bound antibody was determined by gamma scintillation counting. The insert shows the amount of specifically bound antibody as a function of total antibody added. The Scatchard transformation of the binding data as analyzed with the Ligand program is shown in the main graph. The 8B6 Fab bound to a single class of receptors (12,000±per platelet) with a $K_d$ of $5.02\times10^{-8}$M.

A thrombin-activated platelet protein is provided. The protein is selectively expressed on the surface of thrombin-activated platelets. The protein finds use in elucidating the steps involved in the processes of activation, adhesion, and aggregation of platelets.

Two such thrombin-activated platelet proteins are disclosed in the present invention, TAPP-1 and TAPP- 2. TAPP-1 is characterized by a molecular weight of approximately 250 kilodaltons (kd). N-terminal sequencing of the purified protein has revealed that the amino acid sequence is unique when compared with other known proteins. The remainder of the amino acid sequence can be determined by methods known in the art. That is, the antibodies to the protein can be used to isolate the protein and the protein can be sequenced by standard techniques.

TAPP-2 is characterized by a molecular weight of approximately 120 kd, as determined on both denaturing and nondenaturing gels.

TAPP-1 is specifically bound by antibodies or monoclonal antibodies having, in part, the binding specificity of monoclonal antibody 8B6. TAPP-2 is specifically bound by antibodies or monoclonal antibodies having, in part, the binding specificity of monoclonal antibody 12A7. The monoclonal antibody 12A7 has been deposited under the Budapest Treaty in the American Type Culture Collection, Rockville, Md. 20852, U.S.A., designated as HB 11767 with the identification referenced by the depositor as "hybridoma, MAb12A7." Both of these monoclonal antibodies were produced by immunization with thrombin-activated platelets. Hybridomas producing platelet-specific antibodies were identified by radioimmunoassay. Those antibodies which bound specifically to activated platelets were then selected. Subsequent monoclonal antibodies were generated against TAPP-1, which was affinity-purified using MAb 8B6-affinity chromatography. TAPP-2 was affinity-purified using MAb 12A7-affinity chromatography.

Standard reference work setting forth the general principles of immunology include the work of Klein, J. Immunology: The Science of Cell-Non Cell Discrimination, John Wiley & Sons, New York (1982); Kenneth et al., Monoclonal Antibodies, Hybridoma: A New Dimension In Biological Analyses, Plenum Press, New York (1980); Campbell, A., "Monoclonal Antibody Technology", In Laboratory Techniques In Biochemistry and Molecular Biology, 13, Burdon et al., eds., Elsevier, Amsterdam (1984); and Eisen, H. N., in: Microbiology, 3d ed., Davis et al., eds., Harper & Row, Philadelphia (1980).

Both polyclonal and monoclonal antibodies may be employed in accordance with the present invention. Of special interest to the present invention are antibodies or their functional derivatives, which are produced in humans, or are humanized (i.e., nonimmunogenic in a human) by recombinant or other technology. Humanized antibodies may be produced, for example, by replacing an immunogenic portion of an antibody with a corresponding, but nonimmunogenic portion (i.e., chimeric antibodies). See, Robinson et al., International Patent Publication, PCT/US 86/02269; Akira et al., European Patent Application 184,187; Taniguchi, M., European Patent Application 171,496; Morrison et al., European Patent Application 173,494; Neuberger, PCT Application WO 86/01533; Cabilly et al., European Patent Application 125,023; Better, et al., Science 240:1041–1043 (1988); Liu et al., Proc. Natl. Acad. Sci. USA 84:3439–3443 (1987); Liu et al., J. Immunol, 139:3521–3526 (1987); Sun et al., Proc. Natl. Acad. Sci. USA 84:214–218 (1987); Mishimura et al., Cancer Res. 47:999–1005 (1987); Wood et al., Nature 314:446–449 (1985); and, Shaw et al., J. Natl. Cancer Inst. 80:1553–1559 (1988). For general reviews of humanized chimeric antibodies, see, Morrison, S. L. Science 229:1202–1207 (1985) and Ooi et al., BioTechniques 4:214 (1986).

As noted above, an antibody molecule of the present invention includes both monoclonal antibodies and fragments thereof. It may be preferable in some situations to employ the Fab, Fab', F(ab)'$_2$ or Fv fragment of such an antibody in order to minimize any immunological reaction caused by the Fc portion of the immunoglobulin.

The invention is also drawn to the gene for the thrombin-activated platelet protein described herein. This gene region includes the promoter, coding sequence, untranslated sequence, and terminator region. Once a portion of the amino acid sequence of a protein is known, methods are available in the art to construct DNA probes capable of hybridizing to the corresponding gene in a DNA library. To isolate the gene encoding the thrombin-activated platelet protein, a DNA probe sequence can be constructed from the N-terminal amino acid sequence of the protein. Methods for construction of the DNA probe and cloning of a gene are generally available in the art. Similarly, the DNA coding sequence for TAPP (including both TAPP-1 and TAPP-2) may be identified using antibodies to detect recombinant protein in expression libraries. See, for example, Sambrook et al., Molecular Cloning: A Laboratory Manual, 2d ed., Vols. 1–3, Coldspring Harbor Laboratory Press (1989).

Since the protein of the invention is selectively expressed on the surface of thrombin-activated platelets and not on resting platelets, the protein and antibodies which selectively bind thereto are useful for detecting the presence of activated platelets. That is, by determining the presence of TAPP one can determine the presence of a blood clot within a patient. Thus, the antibodies or fragments thereof of the present invention are particularly suited for use in immunoassays. See, Palabrica et al., Proc. Natl. Acad. Sci. USA 86:1036–1040 (1989).

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steriod isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd.

Paramagnetic isotopes for purposes of in vivo diagnosis can also be used according to the methods of this invention. Examples of elements that are particularly useful for use in Magnetic Resonance Energy techniques include $^{157}$Gd, $^{55}$Mn, $^{162}$Dy, $^{52}$Cr, $^{56}$Fe, $^{123}$I, and the like. For discussions on in vivo nuclear magnetic resonance imaging, see, for example, Schaefer et al., JACC 14:472–480 (1989); Shreve et al., Magn. Reson. Med. 3:336–340 (1986); Wolf, G. L., Physiol. Chem. Phys. Med. NMR 16:93–95 (1984); Wesbey et al.,

*Physiol. Chem. Phys. Med. NMR* 16:145–155 (1984); Runge et al., *Invest. Radiol.* 19:408–415 (1984).

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, et al., *Clin. Chim. Acta* 70:1–31 (1976) and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxy succinimide ester method, all these methods incorporated by reference herein.

The invention is also drawn to the use of monoclonal antibodies to TAPP to target immunodiagnostic or immunotherapeutic agents to a blood clot. Methods are available in the art for the linkage of antibodies to other molecules. See, for example, Bode et al., *Science* 229:765–767 (1985) which teaches covalent linkage of urokinase to a fibrin-specific antibody.

Chimeric or hybrid antibodies may also be prepared by recombinant DNA techniques. Such chimeric immunoglobulin molecules have an antigen binding site specific for TAPP linked to a second protein which comprises a therapeutic agent. Methods for preparing chimeric antibodies have been described by Oi and Morrison, *Biotechniques* 4:214 (1986); Morrison *Science* 229:1202 (1985); Neuberger et al., *Nature* 314:268 (1985); European Patent Application 120,694; European Patent Application 125,023; PCT Application WO 83/03971; PCT Application WP 83/01233; Boulianne et al., *Nature* 312:643 (1984); Morrison et al., *Proc. Natl. Acad. Sci. USA* 81:6851 (1984); Sharon et al., *Nature* 309:604 (1984); Neuberger et al., *Nature* 312:604 (1984); Robbins et al., *Biochemistry* 25:3603–3611 (1986); Stump et al., *J. Biol. Chem.* 26:17120–17126 (1986); Nelles, *J. Biol. Chem.* 262:10855–10862 (1987); and Nelles et al., *J. Biol. Chem.* 262:5682–5689 (1987).

In this manner, antibodies, polyclonal or monoclonal, or antibody fragments specific for TAPP may be combined with therapeutic or thrombolytic agents. The term "thrombolytic agent" is meant to refer to any agent capable of dissolving a fibrin-platelet clot, or inhibiting the formation of such a clot. Examples of thrombolytic agents include streptokinase, staphylokinase, prourokinase, urokinase, and tissue-type plasminogen activator. Natural activators or recombinant activators may be utilized. The invention may additionally employ hybrids, physiologically active fragments, mutant or chimeric forms of the above thrombolytic agents including single chain urokinase plasminogen activator (SCU-PA) and active fragments thereof. The term "plasminogen activator" as used herein is intended to include such hybrids, fragments and mutants as well as both naturally derived and recombinantly derived plasminogen activators. See, for example, Stump et al., *J. Biol. Chem.* 261:17120 (1986) and Nelles et al., *J. Biol. Chem.* 262:10855 (1987).) Other potential therapeutic agents include thrombin inhibitors (and their derivatives), activated protein C, factor Xa inhibitors, and other antithrombotic agents.

These therapeutic agents can be used alone or in combination.

This invention is also drawn to the detection of blood clots in vivo. In this application the antibody may be labeled with a radioisotope, an enzyme, a contrast agent, etc.

The antibody/therapeutic agents of the present invention can be formulated according to known methods to prepare pharmaceutically useful compositions such as by admixture with a pharmaceutically acceptable carrier vehicle. Suitable vehicles and their formulation are described, for example, in Remington's Pharmaceutical Sciences (16th ed., Osol, A. Ed., Mack Easton PA (1980)). In order to form a pharmaceutically acceptable composition suitable for effective administration, such compositions will contain an effective amount of a hapten-binding molecule or thrombolytic agent, either alone, or with a suitable amount of carrier vehicle.

Additional pharmaceutical methods may be employed to control the duration of action. Controlled release preparations may be achieved by the use of polymers to complex or absorb the antibody or antibody fragment/therapeutic agents of the present invention. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in Remington's Pharmaceutical Sciences (1980).

It is contemplated that the therapeutic or diagnostic compositions of the present invention will be administered to an individual in therapeutically effective amounts. That is, in an amount sufficient to locate and/or lyse a thrombus. The effective amount of the composition will vary according to the weight, sex, age, and medical history of the individual. Other factors which influence the effective amount may include, but are not limited to, the severity of the patient's condition, the size and extent of the thrombus in a particular individual or target tissue, the kinetics of interactions between the target protein and the therapeutic composition. Generally, the composition will be administered in doses ranging from about 0.01 to about 1 picomoles/ml, preferably from about 1 to 10 picomoles/ml, more generally about 0.001 picomoles/ml to 50 picomoles/ml.

The pharmaceutically prepared compositions of the invention may be provided to a patient by means well known in the art. Such means of introduction include oral means, intranasal means, subcutaneous means, intramuscular means, intravenous means, intraarterial means, or parenteral means.

The antibody/therapeutic agent molecules of the present invention may be dissolved in any physiologically tolerated liquid in order to prepare an injectable bolus. It is preferable to prepare such a bolus by dissolving the molecule in normal saline.

As noted above, an antibody molecule of the present invention includes both monoclonal antibodies and fragments thereof. It may be preferable in some situations to employ the Fab, F(ab'), (Fab')$_2$ or Fv fragment of such an antibody in order to minimize any immunological reaction caused by the Fc portion of the immunoglobulin.

Blood clots which may be treated according to the methods of the invention include, but are not limited to pulmonary thromboembolism, deep venous thrombosis, cerebroembolism, renal vein and peripheral arterial thrombosis, and the like.

The compositions of the present invention are ideally suited for the preparation of a kit. Such a kit may comprise a carrier means being compartmentalized to receive in close confinement one or more container means such as vials, tubes, and the like, each of said container means comprising separate elements of diagnostic or therapeutic agents to be used.

Having now generally described this invention, the same will be better understood by reference to certain specific examples which are included herein for purposes of illustration only, and are not intended to be limiting of the invention, unless specified.

EXAMPLES

In order to further elucidate some of the molecular arrangements which occur in the platelet membrane with thrombin activation, we have produced antibodies which specifically bind to activated platelets. In this study we characterized a monoclonal antibody which bound to a protein selectively expressed on the surface of the thrombin-activated platelets. Two such proteins have been identified: TAPP-1 (by MAb 8B6) and TAPP-2 (by MAb 12A7).

METHODS

Materials were obtained from the following suppliers: affinity purified goat anti(mouse Fab') (GAMFab), Cappel Laboratories (Malvern, PA); Sepharose 2B, PD-10 columns, high and low molecular weight protein standards, Pharmacia (Uppsala, Sweden); pre-stained protein standards and DEAE Affigel Blue, BioRad (Richmond, Calif); Balb/C mice and New Zealand white rabbits, Charles River (Wilmington, Mass); bovine thrombin, Parke-Davis (Morris Plains, N.J.); Freund's adjuvant, Difco (Detroit, Mich); Na$^{125}$I, Amersham (Arlington Heights, Ill); polyvinylidene difluoride transfer membranes, Millipore (Bedford, Mass); trypsin (TPCK-treated), mecuripapain, Triton X100 and RIA-grade bovine serum albumin Sigma (St. Louis, Mo.), DE52 resin, Whatman (Kent, England); magnetic goat-antimouse immunoglobulin particles, Collaborative Research (Bedford, Mass). All other chemicals were of reagent grade or better.

Monoclonal antibody production. To obtain platelets for immunization rabbit blood was collected into 10% citrate (3.8%), and spun at 250$\times$g for 15 minutes to remove red blood cells (rbcs). The platelet-rich plasma was removed and then spun at 1500$\times$g for 20 minutes to separate the platelets from plasma. The platelets were resuspended in HEPES buffered saline (HBS), 2 mM CaCl$_2$ and then recentrifuged for 15 minutes. After aspiration of buffer, the platelets were again suspended in 1.0 ml of HEPES buffered saline with 2 mM CaCl$_2$ and 0.15 units of thrombin and incubated for 30 minutes at 37° C. Female Balb/C mice ($\sim$8 week old) were immunized with 20 $\mu$l of aggregated platelets emulsified in Freund's adjuvant. They were subsequently boosted twice over a 3 month interval. On the three days immediately prior to the fusion, the mice were hyperimmunized with 100 $\mu$l of thrombin-activated platelets intraperitoneally Somatic cell fusion was performed as previously described (Reed et al., Trans. Assoc. Am. Physicians CI:2-50-256 (1988)). The fusion frequency was 90%. Hybridomas producing platelet specific antibodies were identified by a radioimmunoassay. In this assay platelets were obtained from 50 ml of rabbit blood as described above. After resuspension in 1 ml of HBS with 2 mM CaCl$_2$, they were activated with 0.15 units of thrombin. They were then resuspended in 50 ml of HBS, centrifuged at 1000$\times$g for 20 minutes and the supernatant removed; this step was repeated. The aggregated platelets were then diluted into 6 ml of TBSA. For hybridoma screening, 50 $\mu$l of hybridoma supernatant was mixed with 25 $\mu$l of aggregated platelets and incubated in 12$\times$65 mm tubes for 1 hour at room temperature. Subsequently, the platelets were washed with 3 ml of 1% horse serum in TBSA and centrifuged at 2500 rpm for 20 minutes at 4° C. The supernatant was removed. Then 25 $\mu$l of $^{125}$I-GAMFab was incubated with the platelet pellet for 1 hour. The platelets were again washed with 2 ml of 1% TS-TBSA and centrifuged as before. After aspiration of the supernatant, platelet-bound antibody was measured by gamma-scintillation counting. Specific antibody to activated rabbit platelets was detected in 5.4% of the hybridomas. Hybridomas were cloned by limiting dilution.

Antibody purification and fragmentation. Cloned hybridomas were expanded into ascites in mice that had been primed with 0.5 ml of pristane. Ascites was fractionated by precipitation with 40% ammonium sulfate. The precipitate was isolated by centrifugation at 17,000 rpm for 30 minutes at 4° C. The pellet was resuspended in approximately 20% of the initial volume with 0.9% saline and dialyzed into 10 mM sodium phosphate buffer, pH 7.4. After dialysis, the solution was clarified by repeat centrifugation at 17,000 rpm for 30 minutes at 4° C. The supernatant was then passed over a 100 ml DEAE Affigel-Blue column at about 50-75 ml/hr. The bound antibody was eluted by a NaCl gradient of 0-100 mM NaCl in 10 mM phosphate, pH 7.4. Fractions containing antibody were identified by SDS-PAGE and concentrated under pressurized nitrogen gas using an Amicon concentrator.

Fab fragments were prepared by limited papain digestion of whole MAb. Whole MAb was dialyzed into 0.1M NaH$_2$PO$_4$,2 mM EDTA, pH 7.0. Cysteine HCl and papain were added to final concentrations of 0.1M and 1% (of MAb concentration) respectively. After an experiment had revealed the optimal time for papain digestion at 37° C., a preparative digest was performed. The digest was terminated by the addition of iodoacetamide to a final concentration of 1 mg/ml and the digest was dialyzed against 5 mM sodium phosphate, 0.02% NaN$_3$. The digest was passed over a DE52 column which had previously been equilibrated with the same buffer. Fab was collected in the fall-through and whole IgG and Fc eluted by increasing sodium phosphate concentrations. The results of the digest and the subsequent purification were ascertained by SDS-PAGE.

Purified MAb and Fab were radioiodinated by the Iodogen method (Fraker et al., *Biochem. Biophys. Res. Commun.* 80:849–857 (1978)). For each iodination the specific radioactivity was determined in triplicate by paper chromatography in a 50% ethanol-water mixture.

PLATELET BINDING STUDIES a. Comparative Binding of MAb 8B6 to Resting and Thrombin-Activated Platelets. Pooled human platelets were separated from plasma by gel chromatography on Sepharose 2B with modified Tyrode's buffer (without calcium and magnesium ions), (Timmons et al., *Meth. Enzymol.* 169:11–21 (1989)) and counted. After being counted, the platelets were divided and one portion was aggregated by the addition of thrombin (0.15 U/ml) and 2 mM $CaCl_2$ and 1 mM $MgCl_2$. The thrombin-activated platelets were diluted into 200 μl of a modified Tyrode's buffer with calcium (1 mM) and magnesium (2 mM); and resting platelets were diluted in a modified Tyrode's buffer without divalent cations and containing EDTA (1 mM). Radioiodinated MAb 8B6 Fab (20 μl, 180,000 cpm) was added to the thrombin-activated or resting platelets in duplicate and allowed to incubate for 1 hour at room temperature. After washing with 3 ml of the corresponding modified Tyrode's buffer, centrifugation and aspiration, the bound antibody was detected by gamma scintillation counting. Equilibrium and saturation binding studies were conducted using $^{125}I$-8B6 Fab, which was incubated with human platelets for various lengths of time from 1 to 120 minutes. The platelet mixture (50 μl) was then layered onto 1 ml of cold, 20% sucrose (0° C.) and microfuged to separate bound from free antibody. After aspiration of the supernatant, the platelet-bound antibody was counted in a gamma scintillation counter (Micro-Medics). These experiments demonstrated that at room temperature, equilibrium binding was achieved within 10 minutes. Subsequently, saturation binding experiments were performed in 12×65 mm polystyrene tubes that had been previously incubated with 1% bovine serum albumin in TBSA to block nonspecific protein binding sites. To the blocked empty tube was added $5 \times 10^6$ cells in a modified Tyrode's buffer with or without thrombin (0.6 units/ml) and $Ca^{2+}$(2 mM) and $Mg^{2+}$(1 mM) in a volume of 20 μl. To each tube in triplicate was added a tracer amount of radiolabeled 8B6 Fab ($7 \times 10^{-10}$ M) and a variable amount of cold 8B6—Fab (1 nM–0.9 μM). To estimate nonspecific binding, a greater than 100-fold molar excess of cold 8B6 Fab was added to tubes. After incubation at room temperature for 30 minutes, 3 ml of ice-cooled modified Tyrodes buffer was added to each tube. After centrifugation at 3500 rpm for 15 minutes, the unbound antibody was removed by aspiration of the supernatant. Bound antibody was quantitated by γ scintillation counting. Binding data were analyzed using the Ligand program (Munson et al., *Ana. Bioch.* 107:220–239 (1980); McPherson, G.A., "Kinetic, EBDA, Ligand, Lowry (Biosoft, Milltown N.J. (1985)). In these experiments, nonspecific binding, as estimated by greater than a 100-fold molar excess of 8B6 Fab, or by the Ligand estimates, was less than 1%.

b. Comparative Binding of MAb 12A7 to Resting and Thrombin-Activated Platelets. Citrated rabbit blood was centifuged at 200×g for 20 minutes to remove red blood cells. Platelet-rich plasma was applied to Sepharose 2B column prewashed with Tyrode's with 5 mM EDTA and then equilibrated with modified Tyrode's buffer (without calcium and magnesium ions) (Timmons and Hawiger, *J. Methods Enzymol.* 169:11–21 (1989)). Platelets were then separated from plasma proteins by gel chromatography as described. After the platelets had been counted, they were divided into two portions. One portion was aggregated by the addition of thrombin (0.15 U/ml, final), $CaCl_2$ (2 mM) and MgCl (1 mM). The thrombin-activated platelets were diluted to a concentration of $5 \times 10^6$ cells/100 μl and incubated with $^{125}I$-MAb 12A7 (34,000 cpm) in a total volume of 200 μl. Similarly, resting platelets were diluted in Tyrode's without divalent cations and with 1 mM EDTA to a concentration of $3.6 \times 10^7$ cells/100 μl. $^{125}I$-MAb 12A7 was added to the resting platelets, as above. A large molar excess (>100-fold) of nonradioactive MAb 12A7 was added to a parallel tubes as an inhibitor to estimate nonspecific binding. After 45 min. incubation, 2 ml of ice-cold Tyrode's (without divalent cations) was added to each tube and the platelets were immediately centrifuged at 3500 rpm. The supernatant was removed and the platelet-bound antibody was determined by gamma-counting.

Equilibrium saturation binding studies were conducted in a similar manner. Platelets activated by thrombin (0.15 U/ml) were incubated in duplicate with various amounts of $^{125}I$-MAb 12A7 (1,000,000 to 6,250 cpm) in a total volume of 200 μl. Each tube also contained a molar excess (>100-fold) of a control, anti-digoxin MAb, of the same isotype (Mudgett-Hunter et al., *Mol. Immunol.* 22:477–488 (1985)), which was added to inhibit nonspecific binding of $^{125}I$-MAb 12A7 to platelets via Fc receptors. To estimate nonspecific binding, a molar excess (>100-fold) of nonradioactive MAb 12A7 was added to one set of tubes. After incubation for 45 mintues at room temperature 2 ml of cold Tyrode's buffer was added, the tubes were centrifuged at 3000×g for 10 minutes and the unbound $^{125}I$-12A7 MAb was removed. The bound antibody was measured by gamma counting in Micro-Medics 4/600 counter. To study the binding of MAb 12A7 to resting platelets a similar procedure was performed except that the number of platelets had to be increased to $1.29 \times 10^8$ cells in total incubation volume of 400 μl. The platelets were incubated with various amounts of MAb 12A7 (2,000,000 to 25,000 cpm) as above. The binding data was analyzed by the Ligand program of Munson and Rodbard, *Anal. Biochem.* 107:220–239 (1980)). Nonspecific binding in these experiments, as estimated with a greater than 100-fold molar excess of 12A7, or by the Ligand analysis, was less than 1%. The binding of 12A7 to platelets stimulated by different agonists was also studied. Platelets were isolated as described above. Platelets ($5 \times 10^6$ cells/40 Kl) in modified Tyrode's (without divalent cations) were added to plastic tubes. Tyrode's with or without Ca and Mg (40 μl) was added to some tubes; Tyrode's without divalent cations and with EDTA (1 mM) was added to others. Platelets were stimulated with thrombin (0.5 U/ml), ADP (10 uM), epinephrine (2 mM), or A23187 (2 μm) in a final volume of 100 μl. The cells were incubated for 10 minutes at room temperature and then fixed by adding 1/10 volume of 4% paraformaldehyde in 0.1M phosphate buffer, pH 7.2. After 30 minutes the solution was neutralized with an equal volume of 20 mM $NH_4Cl$, 150 mM NaCl, 0.3M Tris, pH 7.2. The platelets were washed with 2 ml of Tyrode's, spun at 3500 rpm for 10 minutes and the supernatant was removed. The platelets were incubated with $^{125}$I-12A7 (50,000 cpm) with or without unlabeled MAb 12A7 (0.5 ug) added as an inhibitor to estimate nonspecific binding. After 45 minutes the platelet samples were again washed, spun, aspirated and gamma-counted.

SDS-PAGE analysis of immunoprecipitates with 8B6 from resting and thrombin-activated platelets. Pooled human platelets were isolated from platelet-rich plasma by differential centrifugation. Platelets to be activated by thrombin were washed twice in HBS, activated by thrombin (0.15 U/ml) and washed with HBS-CaCl$_2$ (2 mM). Resting platelets were washed twice in HBS-EDTA (5 mM). The resting and thrombin-activated platelet pellets were resuspended in trypsin (TPCK-treated, 2.5 mg/ml) and incubated overnight at 37° C. After centrifugation, the supernatant was isolated. A 100 μl aliquot from each was iodinated by the Iodogen method (Fraker et al., *Biochem. Biophys. Res. Commun.* 80:849–857 (1978)). Protein bound radioactivity was isolated by chromatography on a PD-10 column. For immunoprecipitation, 100 μl of MAb 8B6 or a control MAb (anti-digoxin 40–160, Mudgett-Hunter et al., *Mol. Immunol.* 22:455–488 (1985)) was preincubated with 25 μl of goat-antimouse antibody immobilized on magnetic particles. The tubes were washed with 3 ml of PBSA containing 0.5% bovine serum albumin. The immobilized MAbs were then incubated with 20 μl (300,000 cpm) of trypsin-cleaved platelet proteins from resting and thrombin-activated platelets for 3 hours at room temperature. The immunoprecipitates were washed three times with PBSA containing 0.1% lubrol. After solubilization and boiling in sample buffer (Laemmli, U.K. *Nature* 277:680–685 (1970)), the immunoprecipitates were electrophoresed on 10% nonreducing and reducing SDS-polyacrylamide gels. The dried gels were autoradiographed on Kodak XR film.

Cellular labeling and immunoprecipitation with 12A7. Platelets were isolated from 12 ml of platelet-rich plasma (in 1 mM EDTA) by differential centrifugation. Platelets were washed twice with 50 ml of modified Tyrode's with 1 mM EDTA and then once with modified Tyrode's without EDTA or divalent cations. Cells ($8.9 \times 10^8$) were resuspended in 1 ml of Tyrode's with Ca$^{2+}$ and Mg$^{2+}$ and aggregated with 2 units of thrombin. The thrombin-activated cells, or the resting cells were then microfuged at 3000 rpm for 5 minutes. The supernatant was removed and the cells were resuspended in 0.2M potassium phosphate, pH 7.2. The resting or activated platelets were then radioiodinated using coupled glucose oxidase-lactoperoxidase catalysis (Marchalonis, J. J., *Biochem. J.* 113:229 (1969)). The unbound radioactivity was removed by 3 cycles of washing and centrifugation (3000 rpm, 5 minutes). The cellular pellet was then resuspended in modified Tyrode's with or without divalent cations. The cells were lysed by the addition of 0.1% Triton X-100. The iodinated platelet lysates (500,000 cpm) were incubated with 5 μg of purified MAb 12A7 for 1 hr with mixing. Then 25 μl of rabbit anti-mouse antibody coupled to agarose was added to each tube for 30 minutes The agarose was washed with 1 ml of Tris-buffered saline and centrifuged. The supernatant was removed and the agarose was again washed two more times. After the final wash, the agarose was resuspended in 50 μl of sample buffer with 5 μl β-mercaptoethanol and boiled for 5 minutes. The lysate was electrophoresed on 10% SDS-polyacrylamide gels. After drying the gels were autoradiographed.

Affinity purification of TAPP-1 protein. Purified MAb 8B6 (6.3 mg/ml) in PBS pH 8.3, was mixed with CNBr-activated sepharose-4B overnight at 4° C. Approximately 3.6 mg of MAb was coupled per ml of sepharose. Typically, several outdated, random-donor platelet units were pooled, centrifuged, washed and solubilized in Tris-buffered saline (TBS) with 1% Triton X-100, 1 mM CaCl$_2$ and 10 μM leupeptin (Fitzgerald et al., *Anal. Biochem.* 151:169–177 (1985)). The solubilized platelets were centrifuged at 15,000 rpm for 30 minutes at 4° C. The supernatant was then dialyzed against TBS. The samples were then mixed with 8B6-sepharose overnight. The 8B6-sepharose was then washed with TBS, followed by high-salt TBS (0.5M NaCl), followed by TBS with 0.05% lubrol until A280 was less than 0.05. The bound protein was eluted in 5 ml fractions with 0.2M glycine pH 2.7 into tubes containing 1.0M Tris pH 9.0 for neutralization. The affinity-purified protein was subjected to SDS-PAGE analysis and immunoblotting. The eluate was then electrophoresed on both 6% nonreduced or 10% reduced polyacrylamide gels, along with purified MAb and molecular weight standards. Proteins were detected by staining with Coomassie Brilliant Blue dye. Amino-terminal Edman degradation was performed on a sequencer.

Affinity Purification of TAPP-2 Protein. Ascites (17 ml) from hybridoma 12A7 was fractionated by precipitation with 50% ammonium sulfate. The precipitate was isolated by centrifugation at 17,000 rpm for 30 minutes at 4° C. The pellet was resuspended in half of the initial volume and dialyzed against PBS, pH 8.0 and mixed with CNBr-activated Sepharose 4B overnight for 2 hrs. at room temperature and then overnight at 4° C. In the morning the column was washed and incubated with TBSA to block any remaining active sites. Prior to use, the column was pre-eluted with 0.1M glycine, pH 2.9. In typical experiments, platelets were isolated from approximately 200 ml of activated platelet-rich plasma. The platelets were centrifuged and washed three times with TBS pH 7.4 with 2.5 EDTA. The platelet pellet was resuspended in 10 ml of TBS containing 1 mM Ca$^{2+}$, 10 mM leupeptin and 1% Triton X-100. The platelets were centrifuged for 20 minutes at 15,000 rpm and at 4° C. The supernatant was mixed with the MAb 12A7-agarose in a column for 60 minutes. The agarose was washed three times with TBS (15 times the column volume) followed by TBS with 500 mM NaCl until the optical absorption at 280 nm was 0.02. Bound protein was eluted with 0.1M glycine, pH 2.9 into tubes containing 70 μl of 3M Tris pH 9.0 to neutralize the acidity. The eluted protein was subjected to SDS-PAGE (Laemmli, U.K. *Nature* 227:680–685 (1970)) and silver staining. Purified APP was subjected to deglycosylation by endoglycosidase-F. After lyophilization, TAPP-2 was dialyzed into TBS with 1% Triton X-100. Subsequently, EDTA (25 mM), SDS (0.5%), mercaptoethanol (1%) and endoglycosidase (2% of total protein) were added. The digestion was allowed to proceed overnight at 37° C. Digested and undigested TAPP-2 were analyzed by electrophoresis on 10% SDS-gels followed by silver staining. Purified TAPP-2 was subjected to isoelectric focusing on a BioRad 111 Mini ZEF apparatus using ampholytes with a pH range of 3–10.

Immunoblotting. Platelets were isolated from 50 ml of normal rabbit blood by differential centrifugation (Mustard et al., *Meth. Enzymol.* 169:3-11 (1989)). The platelets were resuspended in Hepes-buffered saline with 5 mM EDTA, washed with 50 ml of buffer and centrifuged again. After an additional washing and centrigation, the platelet pellet was dissolved in 500 μl of 10% SDS and boiled for two minutes. The solubilized washed platelets (5 ml) were electrophoresed on 6% polyacrylamide gels using a Laemmli buffer system (Laemmli, U. K. *Nature* 227:680-685 (1970)). The proteins were then transferred to polyvinylidene difluoride (PVDF) membranes by semi-dry electroblotting as described by Khyse-Anderson (*J. Biochem. Biophys. Meth.* 10:203-209 (1984)). The membranes were washed in Tris-buffered saline (0.02% azide) and incubated overnight in 1% albumin at 4° C. to block nonspecific protein binding sites. After washing three times in TBSA, the blots were incubated with purified MAb 8B6 in 0.1% BSA for 1 hour. After an additional three washes, the blots were incubated with a radiolabeled goat-anti(mouse Fab'2) for one hour. The blots were again washed three times and exposed to Kodak Xomat AR film to detect bound antibody. Immunoblotting experiments were also performed with rabbit polyclonal serum specific for the N-terminal sequence of GMP-140/PADGEM in a similar fashion. After washing, the bound rabbit antibody was detected by probing with $^{125}$I-protein A.

Further immunoblotting experiments were performed for TAPP-2 after lysis of cells by sonication, Triton X-100, or Triton-X114. Platelet-rich plasma (15 ml) was divided into 3 equal portions and platelets were isolated by centrifugation as described above. The platelets were resuspended and washed in TBS (2.5 mM EDTA, 100 U/ml aprotinin, and 10 μM leupeptin) and centrifuged. After another cycle of washing, the platelet pellet was resuspended in the same buffer with 1 mM PMSF. One aliquot was sonicated on ice for 1 minute at 100 watts until the suspension clarified. Another platelet aliquot was resuspended in the same buffer with Triton X-100 and the third sample was resuspended in buffer with 1% Triton X-114. Triton X-114 was partitioned into aqueous and detergent phases as described (Hayward et al., *J. Biol. Chem.* 266:7114-7120 (1991)). All samples were centrifuged at 12,000 rpm for 30 minutes in a microcentrifuge. The supernatant of the sonicated platelets, Triton X-100 and the Triton X-114 extracts (aqueous phase) had estimated protein concentrations of 5.9, 7 and 9.3 mg/ml, respectively. Afterwards supernatant from each step was subjected to SDS-PAGE (Laemmli, U.K., *Nature* 227:680-685 (1970)) followed by immunoblotting with MAb 12A7 as described.

RESULTS

1. MAb 8B6 and TAPP-1

After somatic cell fusion, assays revealed that 5.4% of candidate hybridomas produced antibody that specifically bound to rabbit platelets. One of these hybridomas, MAb 8B6 also produced antibody which bound to thrombin-activated human platelets. This hybridoma was cloned by limiting dilution and found to be of the γ1K serotype.

Binding experiments were performed to determine the specificity of binding of MAb 8B6 was resting versus thrombin-activated platelets. Radioiodinated 8B6 Fab was incubated with various numbers of resting and thrombin-activated platelets. When 8B6 was incubated with resting platelets there was minimal, if any, binding of the antibody. In comparison, when 8B6 was incubated with thrombin-activated platelets there was a sharp increase in the amount of antibody bound as a function of platelet number. When these curves were compared, it appeared that MAb 8B6 bound almost exclusively to thrombin-activated platelets (FIG. 1).

To confirm that MAb 8B6 bound preferentially to activated platelets, immunoprecipitation experiments were performed. Platelets were activated with thrombin and then washed to remove secreted proteins that were not bound to the platelet surface. Then resting platelets (in EDTA) or washed, thrombin-activated platelets were incubated with trypsin to cleave bound proteins from the platelet surface. The platelets were centrifuged and the supernatant containing the protein digest was removed. This protein digest was radiolabeled and then immunoprecipitated by MAb 8B6 or an inert, control MAb (anti-digoxin 40-160) (Mudgett-Hunter et al., *Mol. Immunol.* 22:455-488 (1985)) of the same isotype. The immunoprecipitates were washed and subjected to SDS-PAGE and autoradiography. The immunoprecipitates from both MAb 8B6 and the control MAb group show a similar pattern of non-specific binding which was probably due to the second, goat antimouse antibody used for immunoprecipitation. However, compared to the control MAb, MAb 8B6 precipitates an unique band of $M_r$ 94 kd from the thrombin-activated platelets under non-reducing conditions. Under reducing conditions, MAb 8B6 uniquely immunoprecipitates 2 fragments of $M_r$ 42 kd and 36 kd. These results independently confirmed the whole cell binding experiments by demonstrating that MAb 8B6 bound to a (trypsin-cleavable) protein which was selectively expressed on the surface of activated platelets.

Figure 3:
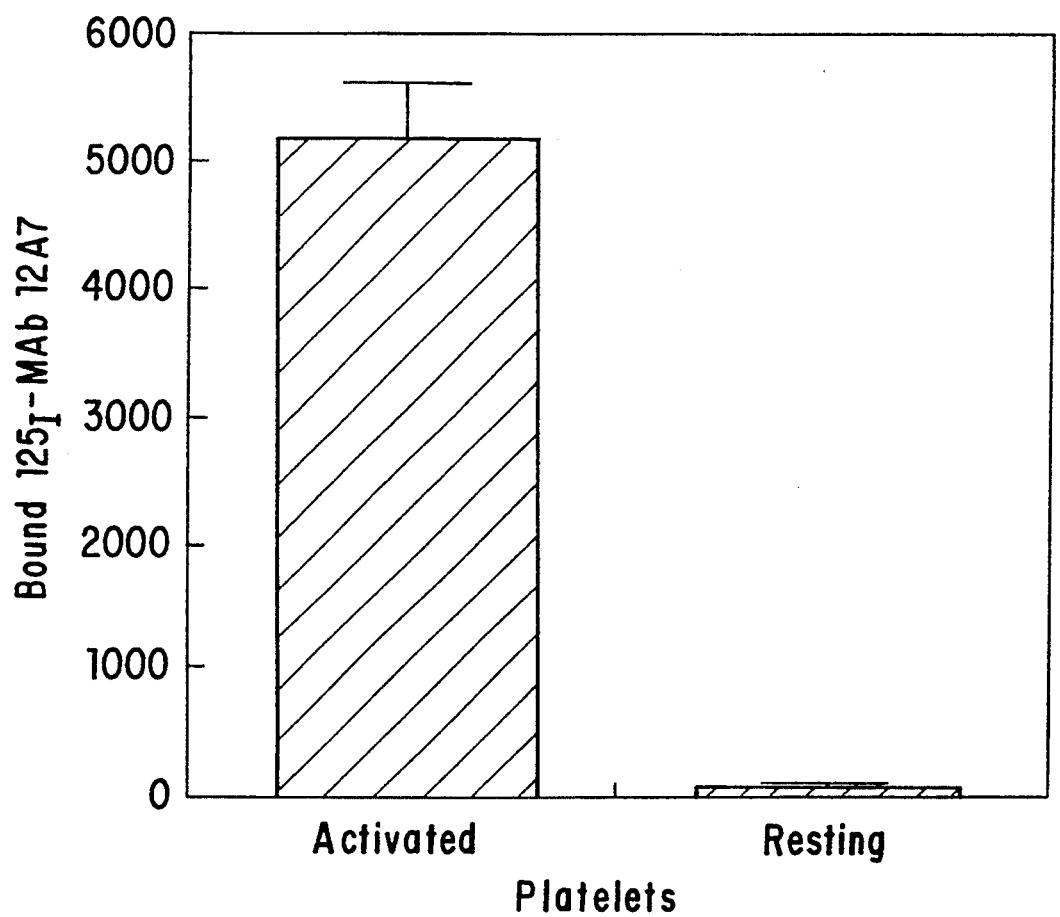
FIG. 3 shows the comparative binding of $^{125}$I-MAb 12A7 to resting and thrombin-activated platelets. Platelets were separated from plasma by gel chromatography and counted. The platelets were divided and one portion was activated with thrombin. The thrombin-activated platelets ($5\times10^6$ cells) and the resting platelets ($3.6\times10^\sim$ cells) were incubated with $^{125}$I-MAb 12A7 for 45 minutes at room temperature. Nonspecific binding was estimated by the addition of a molar excess (>100-fold) of nonradioactive MAb 12A7 as an inhibitor. After washing with 2 ml of the corresponding modified Tyrode's buffer (with or without divalent cations), the unbound antibody was removed by centrifugation and aspiration. The bound antibody was detected by gamma scintillation counting of the platelet pellet. The mean and SE of duplicate observations are shown.

Equilibrium binding studies were performed to determine the number of molecules of TAPP-1 present on activated platelets. After determining the time and thrombin doses necessary for maximal binding, the experiments were performed with both radiolabeled 8B6 Fab alone (a "hot" experiment design) (Munson et al., *Anal. Bioch.* 107:220-239 (1980)) and with a competition ("cold") type of design using unlabeled 8B6 Fab as the competitor. FIG. 3 shows the results from a typical "cold" experiment. Pooled human platelets were incubated with various amounts of $^{125}$I-8B6 Fab for 30 minutes at room temperature. Binding was found to be saturable and inhibited (>99.5%) by an excess of cold 8B6 Fab. Analysis of the binding isothem by the Ligand program (Munson et al., *Anal. Bioch.* 107:220-239 (1980); McPherson, G. A., Kinetic, EBDA, Ligand, Lowry (Biosoft, Milltown JJ) (1985)) showed that 8B6 recognized a single class of binding sites (N=12,000±2060 molecules per platelet) with a dissociation constant of $5.02 \times 10^{-8}$ M ($K_A = 2.00 \pm 0.37 \times 10^7$ M$^{-1}$). Similar results were obtained with saturation binding experiments using only radiolabeled ligand. However, when these experiments were performed in parallel with resting platelets, there was insufficient specific binding to estimate the $K_A$ or number of binding sites.

Immunoblotting of SDS-solubilized whole rabbit platelets was performed to determine the molecular weight of the TAPP-1 antigen in the absence of activation. MAb 8B6 bound to a single protein on unreduced gels of $M_r$ 250 kd. Immunoblots of reduced, SDS-solubilized platelet proteins did not bind MAb 8B6. This suggested that the MAb recognized an epitope that was dependent on disulfide bonds. To confirm that TAPP-1 did not consist of a protein complex which contained GMP-140, we performed immunoblotting experiment with antisera to GMP-140. In these nonreduced blots the GMP-140 antisera bound to a single band of approximately 150 kDa but not to TAPP-1.

The TAPP-1 antigen was purified from detergent extracts of platelets by immunoaffinity chromatography using MAb 8B6. Triton X-100 solubilized platelets were passed over an affinity column with MAb 8B6 immobilized on sepharose. The column was subsequently washed with high salt concentrations and a detergent wash to remove nonspecifically bound proteins. The TAPP-1 protein was then eluted with 0.2M glycine pH 2.7. The purified TAPP-1 was subjected to SDS-PAGE analysis on reduced and non-reduced gels and stained with Coomassie Brilliant Blue dye. From the gel it was determined that the unreduced, purified TAPP-1 protein has a $M_r$ of about 250 kd. An indistinct staining pattern suggested that TAPP-1 was a glycoprotein. Three major sets of bands were identified on the reducing gel of TAPP-1: one at 138 kd, a triplet at approximately 56 kd, and a heavy staining band at about 42 kd. Fainter bands were also identified at ~85 kd and ~34 kd. The ~85 kd band may represent a dimer of the ~42 kd species.

To determine the identity of the TAPP-1 antigen we subjected it to amino-terminal Edman sequence analysis. The sequence which was obtained was compared with known amino acid sequences from GENBANK or EMBL (Devereux, J., et al., *Nucleic Acids Research* 12(1):387–395 (1984)), but no strong sequence homology (>60%) was found. Similarly, when the amino acid sequence was back-translated into all possible nucleotide sequences and compared with reported nucleotide sequences, no strong homology could be found. Thus it appears that the TAPP-1 antigen contains a hitherto unreported amino acid sequence.

2. MAb 12A7 and TAPP-2

Hybridomas which produced antibody that specifically bound to rabbit platelets were fully tested to determine whether their binding to platelets was inhibited by plasma proteins. One of these hybridomas, 12A7, bound to activated platelets and was not significantly inhibited by plasma. Comparative whole platelet binding experiments were performed to determine whether the antigen, recognized by MAb 12A7, was differentially expressed by resting and activated platelets. Purified, radioiodinated MAb 12A7 was incubated with resting and thrombin-activated platelets (FIG. 3). When 12A7 was incubated with resting platelets ($3.6 \times 10^7$ cells), there was minimal, if any, antibody binding. In comparison, when 12A7 was incubated with thrombin-activated platelets ($5 \times 10^6$ cells), there was a marked increase in the amount of antibody bound. This suggested that MAb 12A7 recognized an activated platelet protein (TAPP-2) or antigen that was chiefly expressed on the platelet surface after cellular activation by thrombin.

Cellular labelling experiments were performed to confirm the observation that MAb 12A7 bound preferentially to activated platelets. The surface proteins of resting and activated platelets were radioiodinated. Then platelets were lysed with Triton X-100 and the lysate was immunoprecipitated by MAb 12A7. The immunoprecipitates were then electrophoresed on SDS-polyacrylamide gels. Using this technique, TAPP-2 was detected on the surface of activated platelets, but not on resting platelets.

Cellular binding experiments were performed to determine if the expression of TAPP-2 on the platelet membrane could be provoked by different agonists, and if its expression required the presence of extracellular $Ca^{2+}$. FIG. 4 shows that, compared to resting platelets, stimulation of the cells with ADP (10 $\mu$M), A23187 (2 $\mu$M), and thrombin (0.5 U/ml) causes a notable increase of TAPP-2 expression as indicated by the binding of $^{125}$I-MAb 12A7. However, epinephrine (2 $\mu$M) appears to have had little, if any, effect. Extracellular $Ca^{2+}$ does not appear to be critical for the expression of TAPP-2 by thrombin; there is significant binding of $^{125}$I-MAb 12A7 to platelets activated in the absence of added $Ca^{2+}$ as well as in the presence of EDTA as a $Ca^{2+}$ chelator. At the doses of agonists tested in this experiment, thrombin was the most potent agent for inducing expression of TAPP-2 on platelets.

Equilibrium binding studies were performed to determine the number of molecules of the activated platelet protein (TAPP-2) present on activated platelets. After the time and thrombin doses necessary for maximal binding had been determined, studies were performed both with radiolabeled MAb 12A7 in a typical "hot" experimental design (Munson and Rodbard, *Anal. Biochem.* 107:220–239 (1980)). An excess of unlabeled 12A7 was added to duplicate tubes in parallel to estimate nonspecific binding. The binding of MAb 12A7 to platelets was found to be saturable and inhibitable (99%). Since the number of 12A7 binding sites to resting platelets was relatively low (see FIG. 3), it was necessary to use greater than 100-fold more resting platelets per tube than when activated platelets were studied. The binding data was analyzed using the Ligand program (Munson and Rodbard, *Anal. Biochem.* 107:220–239 (1980)). The Scatchard transformation of the data is shown in FIG. 5. MAb 12A7 recognized a single class of binding sites which was present at $14,200 \pm 1100$ molecules per activated platelet and $290 \pm 30$ molecules per resting platelet. The calculated association constant for antibody binding to activated platelets was $6.44 \pm 0.66 \times 10^8 M$.

Earlier experiments had shown that TAPP-2 could not be detected in significant amounts on the surface of resting platelets. This suggested that TAPP-2 may be an intracellular protein prior to cellular activation. Consequently we performed immunoblotting experiments on detergent-lysed resting platelets. After electrophoresis under denaturing conditions, platelet lysates were transferred to polyvinylidene difluoride membranes and probed with MAb 12A7. Immunoblots showed that MAb 12A7 identified TAPP-2 as a single band of $M_r \sim 120$ kd. This molecular mass is the same as that immunoprecipitated by MAb 12A7 from the lysates of radiolabeled activated platelets.

To determine whether TAPP-2 may reside in the membrane or cytosolic cell fractions, platelets were lysed by sonication, Triton x-100 or Triton X-114. Immunoblotting was performed to detect the presence of TAPP-2 in the supernatant from each of these lysates. TAPP-2 was not detected in the supernatant after ultrasonic lysis, but could be easily detected in the supernatant after detergent lysis by Triton X-100 and by Triton x-114 (lane 2–4). Thus TAPP-2 partitions into the detergent fractions in a manner most consistent with a hydrophobic, membrane-associated protein.

TAPP-2 was subsequently was purified from detergent extracts of resting platelets by immunoaffinity chromatography. Detergent-solubilized platelets were passed over an affinity column with MAb 12A7 immobilized on Sepharose. The column was washed with high-salt buffer and a detergent to remove nonspecifically bound proteins. Protein was then eluted with 0.2M glycine, pH 2.7. The eluted protein was then subjected to analytic SDS-PAGE analysis under reducing conditions, followed by silver staining, which showed that purified, reduced TAPP-2 has a molecular weight of ~120 kd. The mean (±S.D.) reduced molecular mass from 3 experiments was 117±7 kd. The mean (±S.D.) molecular mass of the unreduced protein was 109±5 kd (6 experiments). TAPP-2 appears as a sharp band after silver-staining and immunoblotting, suggesting that it is not extensively glycosylated. When TAPP-2 was subjected to overnight digestion by endoglycosidase F, its molecular weight decreased by only 14 kd (118 to 104 kd). Purified TAPP-2 was found to have a pI of 6.0-6.5.

DISCUSSION

1. MAb 8B6 and TAPP-1

We have generated a monoclonal antibody, 8B6, to a novel protein antigen present on the surface of thrombin-activated platelets. This thrombin-activated platelet protein (TAPP-1) was immunopurified and amino terminal amino acids were sequenced. It was found to contain a hitherto undescribed amino acid sequence. From SDS-PAGE analysis, TAPP-1 appears to be a complex of $M_r \sim 250$ kd. Preliminary data suggested that TAPP-1 was composed of 3 chains which are disulfide linked. One chain of ~138 kd appears from its staining pattern to be a glycoprotein. The next largest chain(s) consist of a triplet at an average $M_r \sim 56$ kd. The smallest chain appeared t be ~42 kd.

Recently, other investigators have identified proteins that are selectively expressed on the surface of activated proteins (Nieuwenhuis et al., "The Use of a Panel of Monoclonal Antibodies in the Detection of Activated Platelets," in ASH Satellite Symposium, Atlanta, Ga. (1989); Hayward et al., *Blood* 76 (Suppl. 1):458A (1990); Hsu-Lin et al., *J. Biol. Chem.* 259:9121-9126 (1984); and McEver, G. A., *J. Biol. Chem.* 259:9799-9804 (1984)). The best characterized of these is GMP-140 or PAD-GEM protein (McEver, G. A., *J. Biol. Chem.* 259:9799-9804 (1984)). Interestingly, on reduce SDS-PAGE analysis, one chain of TAPP-1 has a comparable, but not identical molecular mass (138 kd) to PAD-GEM/GMP-140 (148 kd) (McEver, G. A., *J. Biol. Chem.* 259:9799-9804 (1984); and Hsu-Lin et al., *J. Biol. Chem.* 259:9121-9126 (1984)). However, on nonreduced SDS-PAGE TAPP-1 migrates as a single band of $M_r \sim 250$ which is distinctly different than the 138 kd which is reported for GMP-140/PADGEM protein. In addition, polyclonal antisera to the N-terminal sequence of GMP-140/PADGEM do not cross-react with TAPP-1. Finally, the amino acid sequence obtained from TAPP-1 is different from that reported for GMP-140/PADGEM protein (Johnston et al., *Cell* 56:1033-44 (1989)). None of the other reported activation-dependent antigens in human platelets have a molecular mass similar to TAPP-1 (Nieuwenhuis et al., "The Use of a Panel of Monoclonal Antibodies in the Detection of Activated Platelets," in ASH Satellite Symposium, Atlanta, Ga. (1989); Gralnick et al., *Blood* 76 (Suppl 1):457A (1990); and Hayward et al., *Blood* 76 (Suppl. 1):458A (1990)).

The mechanism by which TAPP-1 becomes expressed on the surface of activated platelets is unclear. It is possible that the antigen represents a combination of two proteins which become bound together after platelet aggregation. This creation of a new protein epitope by the binding of two or more molecules has been referred to as "receptor-induced binding site" or "ligand-induced binding site" by Frelinger et al. (*J. Biol. Chem.* 265:6346-6352 (1990)). Alternatively, the antigen may be created after thrombin-activation as a result of an enzyme modification of an existing platelet protein. This phenomenon, which might be dubbed "enzyme created epitope", has been exploited to generate specific MAbs (Hui et al., Science 22:21129-1131 (1983); Lukacova et al., *Inhibition Of Factor XIII Activation By An Anti-Peptide, Monoclonal Antibody*:unpublished (1991)). However, since binding studies with resting whole platelets failed to detect significant quantities of TAPP-1 (which was detected by immunoblots of solubilized, resting whole platelets), it appears that the protein is present in the platelet and becomes available only after activation and secretion, like GMP-140/PADGEM.

Glycoproteins have been shown to play many functional roles in platelets. Some, like GPIIb/IIIa or GPIb, bind protein ligands which are necessary for aggregation or adhesion. Others have been demonstrated to be "true" receptors for platelet agonists, e.g., aggregin (Coleman, R. W. *Hematology/Oncology Clinics of North America*:27-42 (1990)). Still other proteins have been shown to represent binding sites for proteins like thrombin but their significance remains unclear (e.g., GPV). Activation-dependent platelet antigens may also represent a means of signalling of interacting with other vascular cells as may be the case with GMP-140/PAD-GEM. At present we do not know the functional significance of TAPP-1, not have exhaustive experiments been performed to determine whether the protein is expressed on platelets that are stimulated by agonists other than thrombin. Studies to answer these questions are in progress.

Cellular activation-dependent antigens provide a potent method for the discriminative study of resting and activated platelets in vitro. In addition, antibodies or other probes which identify these antigens may be useful for identifying or targeting platelet thrombi in vivo. Since it appears that the platelet density or number of some activation dependent antigens change with platelet age (Savage et al., *Blood* 74:1007-1014 (1989)), it may be possible to exploit these changes to study the molecular alternations that occur in platelet thrombi over time.

2. MAb 12A7 and TAPP-2

We have generated a monoclonal antibody that identifies an ~120 kd protein antigen that can be readily detected on the surface of platelets after cellular activation by ADP, A23187, and thrombin. Whole-cell binding experiments revealed that TAPP-2 was present in trace amounts on resting platelets (~300 molecules/cell) and that its expression increased by nearly 50-fold after platelet activation by thrombin. When the external platelet membrane proteins were radiolabeled, TAPP-2 could only be detected by autoradiography in immunoprecipitates from platelets after activation. However, when resting whol platelets were solubilized in detergent, TAPP-2 could be detected by immunoblotting. When cells were lysed by sonication, TAPP-2 was not released into the aqueous supernatant. However, after lysis by Triton X-100 and Triton X-114, TAPP-2 was extracted by the detergent into the supernatant. This pattern is typical of membrane-associated proteins.

Three types of platelet activation antigens have been identified by MAbs (see Abrams and Shattil, 1991 for a review). The first type of platelet activation antigen assumes an unique conformation as a result of platelet activation, or of binding to a receptor or to a ligand (e.g., Frelinger, et al., *J. Biol. Chem.* 265:6346–6352 (1990)). The MAb recognizes this unique conformation and thus binds to activated platelets. Examples of this type of activation antigen include fibrinogen and the glycoprotein IIb/IIIa molecules. However, since MAb 12A7 binds to TAPP-2 alone, in the absence of other proteins, even after TAPP-2's conformation has been disrupted by SDS, it seems unlikely that TAPP-2 would represent this type of activation antigen.

Another type of platelet activation antigen is released by platelets and becomes bound to the platelet membrane after activation. Typically these proteins are also found in the plasma in small concentrations (e.g., thrombospondin, Factor V, etc.). TAPP-2 does not appear to be this type of antigen because our experiments indicate that it is not present in the plasma in appreciable concentrations. In addition, TAPP-2 was not detected in the aqueous phase after cell sonication; rather it appeared to require detergents for solubility.

The third type of activation antigen is a protein which becomes bound to the external membrane surface of platelets after granular fusion (see Table I). Like many of these proteins, TAPP-2 appears to require detergent for solubility, and its expression is most potently induced on platelet membranes after activation by thrombin. To determine the identity of TAPP-2 we compared its molecular characteristics to the characteristics of other platelet activation antigens of this type (Table I).

TAPP-2 is closest in molecular mass to two other single chain proteins, LAMP-I and GMP-140. However, TAPP-2 is notably different from LAMP-I in the number of molecules of expressed per activated platelet: 14,200 vs. 1200–2200, respectively. In addition, unlike LAMP-I, TAPP-2 does not appear to be sensitive to extracellular $CA^{2+}$ for expression by thrombin. In further contrast to LAMP-I, TAPP-2 can be elicited by ADP, it does not appear to show the same amount of heterogeneity in molecular mass and its pI is significantly less acidic. Activated platelets express a similar number of copies of TAPP-2 and GMP-140 per cell. However, there is a notable difference between TAPP-2 and GMP-140 in molecular mass. Further, unlike GMP-140, TAPP-2 did not show any significant binding to epinephrine-stimulated platelets (Hsu-Lin, et. al. 1984). Taken together, these differences between TAPP-2 and other platelet activation antigens suggest that TAPP-2 may be a previously obscure platelet protein.

TABLE I

| Antigen | Platelet Activation Antigens | | |
|---|---|---|---|
| | Molecular Mass (kDa) Unreduced, (Reduced) | Binding Sites/Platelet Activated | Resting |
| GMP-140 (PADGEM)[1] | 140 (150) | ~10,000 | <1000 |
| LAMP-1[2] | 110–120 | 1,200 | ≦90 |
| CD-63[3] | 30–60 (30–60) | 12,600 | 650 |
| P-155[4] | 155- Multimeric | 4,100 | 600 |
| Granulophysin[5] | 40 (40) | — | — |
| TAPP-1[6] | 250 (138,56,42) | ~10,000 | — |
| TAPP-2 | 110 (120) | 14,200 | 300 |

[1]Hsu-Lin et al., J. Biol. Chem. 259:9121–9126 (1984); McEver and Martin, J. Biol. Chem. 259:9799–9804 (1984);
[2]Febbraio and Silverstein, J. Biol Chem. 265:18531–18537 (1990);
[3]Nieuwenhuis et al., Blood 70:838–845 (1987);
[4]Hayward et al., J. Biol. Chem. 266:7114–7120 (1991);
[5]Gerrard et al., Blood 77:101–112 (1991);
[6]present invention.

External membrane proteins play many functional roles in platelets. Some, like GPIIb/IIIa and GPIb, bind protein ligands necessary for aggregation or adhesion. Others, are receptors for platelet agonists like ADP or thrombin (Coleman, R.W., *Hematology/Oncology* Clin. N. Am.4:27–42 (1990); Vu et al; *Cell* 64:1057–1068 (1991)). Still other proteins have been shown to represent binding sites for proteins like thrombin, but their significance remains unclear (e.g. GP-V). Given their unique expression on activated platelets, activation-dependent antigens may represent a means by which platelets signal to or interact with other vascular cells, as has been suggested for GMP-140/PADGEM (Larsen et al., *Cell* 59:305–312 (1989)).

Although at present we do not know the purpose for TAPP-2, its near absence on resting platelets and prominent expression on thrombin-activated cells suggests that it plays an important functional role. As exemplified by the research on T-cell specific antigens, the study of platelet activation antigens may provide further insights into cellular function and interaction. Probes that identify these platelet activation antigens may be useful for identifying or targeting platelet thrombi in vivo, and may provide a means of studying the complex interactions that occur between platelets and other cells in processes like wound healing and atherosclerosis.

Hybridoma cell line 8B6 was deposited with ATCC, Rockville, MD, on Sep. 16, 1991, and is assigned the deposit number HB10870. HB10870 was converted to a deposit under the Budapest Treaty on Oct. 1, 1992.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed:

1. A substantially purified protein which is selectively expressed on the surface of thrombin-activated platelets, thrombin-activated platelet protein-2(TAPP-2), said protein having a molecular weight of about 120 kd, and recognized by an antibody having the binding specificity of 12A7.

2. The protein of claim 1, wherein said protein is human TAPP-2.

* * * * *

UNITED STATES PATENT AND TRADEMARK OFFICE
CERTIFICATE OF CORRECTION

PATENT NO. : 5,446,132
DATED : Aug. 29, 1995
INVENTOR(S) : Guy L. Reed, et al

It is certified that error appears in the above-identified patent and that said Letters Patent is hereby corrected as shown below:

On title page, item [63], "Oct. 1, 1992" should read --Oct. 1, 1991--

Signed and Sealed this

Third Day of February, 1998

Attest:

BRUCE LEHMAN

*Attesting Officer*    *Commissioner of Patents and Trademarks*